US007812197B2

(12) United States Patent
Sodervall et al.

(10) Patent No.: US 7,812,197 B2
(45) Date of Patent: Oct. 12, 2010

(54) METHOD FOR THE PREPARATION OF THERAPEUTICALLY VALUABLE TRIPHENYLBUTENE DERIVATIVES

(75) Inventors: Marja Sodervall, Oulu (FI); Maire Eloranta, Oulu (FI); Arja Kalapudas, Oulu (FI)

(73) Assignee: Hormos Medical Ltd., Turku (FI)

( * ) Notice: Subject to any disclaimer, the term of this patent is extended or adjusted under 35 U.S.C. 154(b) by 311 days.

(21) Appl. No.: 12/030,420

(22) Filed: Feb. 13, 2008

(65) Prior Publication Data

US 2008/0207956 A1    Aug. 28, 2008

Related U.S. Application Data

(60) Provisional application No. 60/889,838, filed on Feb. 14, 2007.

(51) Int. Cl.
C07C 41/01    (2006.01)
(52) U.S. Cl. .................................................... 568/641
(58) Field of Classification Search .................. None
See application file for complete search history.

(56) References Cited

U.S. PATENT DOCUMENTS

| | | | |
|---|---|---|---|
| 4,177,121 A | 12/1979 | Ando et al. |
| 4,656,187 A | 4/1987 | Black et al. |
| 4,696,949 A | 9/1987 | Toivola et al. |
| 4,894,373 A | 1/1990 | Young |
| 4,935,243 A | 6/1990 | Borkan et al. |
| 4,996,225 A | 2/1991 | Toivola et al. |
| 5,118,667 A | 6/1992 | Adams et al. |
| 5,189,212 A | 2/1993 | Ruenitz |
| 5,192,525 A | 3/1993 | Yang et al. |
| 5,196,435 A | 3/1993 | Clemens et al. |
| 5,352,699 A | 10/1994 | Jackson |
| 5,446,203 A | 8/1995 | McNelis |
| 5,470,883 A | 11/1995 | Stromberg |
| 5,491,173 A | 2/1996 | Toivola et al. |
| 5,567,714 A | 10/1996 | Bruns |
| 5,658,931 A | 8/1997 | Bryant et al. |
| 5,691,355 A | 11/1997 | Bryant et al. |
| 5,693,674 A | 12/1997 | Bitonti |
| 5,719,136 A | 2/1998 | Chwalisz et al. |
| 5,747,059 A | 5/1998 | Korsgaard et al. |
| 5,750,576 A | 5/1998 | DeGregorio et al. |
| 5,807,899 A | 9/1998 | Bohlmann et al. |
| 5,821,254 A | 10/1998 | Sporn et al. |
| 5,827,892 A | 10/1998 | Loser et al. |
| 5,852,059 A | 12/1998 | Thompson |
| 5,877,219 A | 3/1999 | Willson |
| 5,912,273 A | 6/1999 | DeGregorio et al. |
| 6,037,379 A | 3/2000 | Harkonen et al. |
| 6,245,342 B1 | 6/2001 | Golz-Berner et al. |
| 6,245,352 B1 | 6/2001 | Arbuthnot et al. |
| 6,245,819 B1 | 6/2001 | Halonen et al. |
| 6,525,084 B2 | 2/2003 | Rasmussen et al. |
| 6,576,645 B1 | 6/2003 | Sodervall et al. |
| 6,632,447 B1 | 10/2003 | Steiner et al. |
| 6,875,775 B2 * | 4/2005 | Sodervall et al. ............ 514/317 |
| 6,984,665 B2 | 1/2006 | Blom et al. |
| 2001/0034340 A1 | 10/2001 | Pickar |
| 2004/0248989 A1 | 12/2004 | Santti et al. |
| 2005/0182143 A1 | 8/2005 | Anttila |
| 2005/0187302 A1 | 8/2005 | Blom |
| 2005/0215528 A1 | 9/2005 | Furuya et al. |
| 2007/0104742 A1 | 5/2007 | Lehtola et al. |
| 2007/0197664 A1 | 8/2007 | Steiner et al. |
| 2007/0203180 A1 | 8/2007 | Hoekstra et al. |

FOREIGN PATENT DOCUMENTS

| | | |
|---|---|---|
| EP | 0 095 875 A3 | 12/1983 |
| EP | 0 664 124 A1 | 7/1995 |
| EP | 0 779 808 B1 | 8/1999 |
| EP | 0 760 651 B1 | 7/2001 |
| EP | 1 125 582 A2 | 8/2001 |
| WO | WO 92/06068 A1 | 4/1992 |
| WO | WO 93/19746 A1 | 10/1993 |
| WO | WO 95/26720 A1 | 10/1995 |
| WO | WO 96/07402 A1 | 3/1996 |
| WO | WO 96/35417 A1 | 11/1996 |
| WO | WO 96/40616 A1 | 12/1996 |
| WO | WO 97/32574 A1 | 9/1997 |
| WO | WO 99/42427 A1 | 8/1999 |
| WO | WO 99/63974 A2 | 12/1999 |
| WO | WO 01/36360 A1 | 5/2001 |
| WO | WO 01/54699 A1 | 8/2001 |
| WO | WO 02/07718 A1 | 1/2002 |
| WO | WO 02/090305 A1 | 11/2002 |
| WO | WO 03/047504 A2 | 6/2003 |

(Continued)

OTHER PUBLICATIONS

U.S. Appl. No. 12/030,415, filed Feb. 13, 2008, Marja Sodervall et al.
B.H. Mitlak et al., "Selective Estrogen Receptor Modulators," Drugs 57(5):653-663, May 1999.
Budavari, S. et al., eds., The Merck Index. Eleventh Edition, p. 1430, No. 9019, Merck & Co., Inc., Rathway, NJ, USA (1989).
Dimaraki et al. (European Journal of Endocrinology, vol. 150, pp. 481-487; 2004).
Ferguson et al., Alkali Metal Ion Mediated Cyclization of 4,4'-(3,6-dioxaocta-1,8-diyloxy)-bis(benzophenone), Tetrahedron Letters, Jun. 1993, vol. 34, No. 23, pp. 3719-3722.

(Continued)

Primary Examiner—Rosalynd Keys
(74) Attorney, Agent, or Firm—Brinks Hofer Gilson & Lione

(57) ABSTRACT

The present invention concerns a method for the preparation of therapeutically valuable triphenylbutene derivatives, especially ospemifene or fispemifene.

12 Claims, No Drawings

FOREIGN PATENT DOCUMENTS

| WO | WO 03/103649 A1 | 12/2003 |
| WO | WO 2005/079777 A1 | 9/2005 |

OTHER PUBLICATIONS

G.K. Bolhuis, K. Zuurman, G.H.P. te Wierik; Improvement of dissolution of poorly soluble drugs by solid deposition on a super disintegant. II The choice of super disintegrants and effect of granulation; European Journal of Pharmaceutical Sciences; 1997; 63-69; Elsevier Science B.V.

Goldstein, S.R. et al.; "A pharmacological review of selective oestrogen receptor modulators," Human Reproduction Udate 6:212-224, Oxford university Press (May-Jun. 2000).

Grodstein, F. And Stampfer, M.J., "Estrogen for women at varying risk of coronary disease," Maturitas 30:19-26, Elsevier Science Ireland Ltd. (1998).

Henderson, V.W., "Estrogen, Cognition, and a Woman's Risk of Alzheimer's Disease," The American Journal of Medicine 103:11S-18S, Excerpta Medica, Inc. (1997).

International Search Report for International Application No. PCT/FI00/00946, mailed Feb. 8, 2001.

Jordan, V. Craig; "Antiestrogens and Selective Estrogen Receptor Modulators as Multifunctional Medicines, 2. Clinical Considerations and New Agents," Journal of Medicinal Chemistry, Vo. 46, No. 7, Mar. 27, 2003, pp. 1081-1111.

K.C. Baynes et al., "Selective oestrogen receptor modulators: a new paradigm for HRT," Curr. Opin Obstet Gynecol 10(3): 189-192, Jun. 1998.

Kangas, L. et al., "A new triphenylethylene compound, Fc-1157a: II. Antitumor effects," Cancer Chemother. Pharmacol. 17:109-113, Springer-Verlag (1986).

Kangas, L. et al., "Bioluminescence of Cellular ATP: A New Method for Evaluating Cytotoxic Agents In Vitro," Medical Biology 62:338-343, Duodecim (1984).

Kangas, L., "Biochemical and pharmacological effects of toremifene metabolities," Cancer Chemother. Pharmacol. 27:8-12, Springer-Verlag (Apr. 1990).

Kauffman, Raymond F., et al., "Selective Estrogen Receptor Modulators," Drug News & Perspectives 1995 8 (9) pp. 531-539.

Khovidhunkit, W. and Shoback, D.M., "Clinical Effects of Raloxifene Hydrochloride in Women," Ann. Intern. Med. 130:431-439, American College of Physicians (Mar. 1999). Lobo, R.A., "Benefits and risks of estrogen replacement therapy," Am. J. Obstet. Gynecol. 173:982-989, Mosby-Year Book, Inc. (1995).

Lobo, R.A., "Benefits and risks of estogren replacement therapy," Am. J. Obstet. Gynecol. 173:982-989, Mosby-Year Book, Inc. (1995).

M. Whitehead, "Treatments for menopausal and post-menopausal problems: present and future," Baillieres Clin Obstet Gynaecol 10(3): 515-530, Sep. 1996 (online abstract).

M.M. Kennedy, "Tamoxifen and the endometrium: review of 102 cases and comparison with HRT-related-and non-HRT-related endometrial pathology," Int J Gynecol Pathol 18(2): 130-137, Apr. 1999 (online abstract).

M.W. DeGregorio et al., "Hormone replacement therapy and breast cancer: revisiting the issues," J AM Pharm Assoc. 38(6): 738-744, Nov.-Dec. 1998, (online abstract).

Macgregor, J.I. and Jordan, V.C., "Basic Guide to the Mechanisms of Antiestrogen Action," Pharmacol. Rev. 50:151-196, Williams and Wilkins Co. (1998).

Merriam-Webster's Medical Dictionary (c) [online], Merriam-Webster, Inc., 2002 [retrieved on May 20, 2008]. Retrieved from the Internet: <URL: http://dictionary.reference.com/browse/therapeutic>.

Odeku Oluwatoyin A., Fell, John T.; Effects of the method of preparation on the compression, mechanical, and release properties of Khaya gum matrices; Pharmaceutical development and technology; 2006; vol. 11; 435-436, abstract only.

Peng, Z. et al., "The Mechanical Strength of Bone in Different Rat Models of Experimental Osteoporosis," Bone 15:523-532, Elsevier Science Ltd. (1994).

Plouffe, L., "Selective Estrogen Receptor Modulators (SERMs) in Clinical Practice," J. Soc. Gynecol. Investig. 7:S38-S46, Elsevier Science Inc. (Jan.-Feb. 2000).

Porter, Christopher J. H., et al., "Lipid Based Formulations for Oral Administration," Journal of Receptor & Signal Transduction Research, 21 (2&3) 215-257 (2001).

Qu, Q. et al., "Selective Estrogenic Effects of a Novel Triphenylethylene Compounds, FC1271a, on Bone, Cholesterol Level, and Reproductive Tissues in Intact and Ovariectomized Rats," Endocrinology 141: 809-820, Association for the Study of Internal Secretions (Feb. 2000).

Quinton Singh, Hiren Patel, Mohamed Cassim; Comparative Evaluations of Tablet Formulations; Rhodes University, School of Pharmaceutical Sciences, Department of Pharmaceutics, Rhodes University, Grahamstown, 6140, RSA; www.ru.ac.za/academic/departments/pharmacy/jrats/vol1_1/poster6/tablet8.html; printed Dec. 3, 2007; 1-6.

S.K. Voipio, et al., "Effects of ospemifene (FC-1271a) on uterine endometrium, vaginal maturation index, and hormonal status in healthy postmenopausal women." Maturitas vol. 43, 207-214 (2002).

Salvolainen-Peltonen et al.; "Selective Estrogen Receptor Modulators Prevent Neointima Formation After Vascular Injury"; Molecular and Cellular Endocrinology, vol. 227, 2004, pp. 9-20.

Simberg, N.H. et al, "In Vitro and In Vivo Binding of Toremifene and Its Metabolites in Rat Uterus," Steroid Biochem. vol. 36: 197-202, Pergamon Press plc (1990).

SJ Laight, PCM Mossop, MC Wilkinson; Comparative evaluation of two aspirin formulation techniques; www.ru.ac.za/academic/departments/pharmacy/jrats/vol 1_1/poster5/tablet2.html; printed Dec. 3, 2007; 1-6.

Terenius, L., "Structure-Activity Relationships of Anti-Ostrogens With Regard to Interaction With 17β-Oestradiol in the Mouse Uterus and Vargina," Acta Endocrinol. 66:431-447, Scandinavian University Press (1971). Mar.

The American Heritage © Science Dictionary [online], Houghton Mifflin Company, 2002 [retrieved on May 20, 2008]. Retrieved from the Internet: URL: http://dictionary.reference.com/browse/metabolite>.

* cited by examiner

METHOD FOR THE PREPARATION OF THERAPEUTICALLY VALUABLE TRIPHENYLBUTENE DERIVATIVES

CROSS REFERENCE TO RELATED APPLICATIONS

This application claims priority to U.S. Patent Provisional Patent Application No. 60/889,838 filed Feb. 14, 2007, hereby incorporated by reference.

BACKGROUND

1. Field of the Invention

This invention relates to the preparation of two triphenylbutene derivatives, valuable in therapy as selective estrogen receptor modulators.

2. Description of Related Art

The publications and other materials used herein to illuminate the background of the invention, and in particular, cases to provide additional details respecting the practice, are incorporated by reference.

"SERMs" (selective estrogen receptor modulators) have both estrogen-like and antiestrogenic properties (Kauffman & Bryant, Drug News Perspect. 8:531-539, 1995). The effects may be tissue-specific as in the case of tamoxifen and toremifene which have estrogen-like effects in the bone, partial estrogen-like effect in the uterus and liver, and pure antiestrogenic effect in breast tissue. Based on the published information, many SERMs are more likely to cause menopausal symptoms than to prevent them. They have, however, other important benefits in elderly women: they decrease total and LDL cholesterol, thus minimizing the risk of cardiovascular diseases, and they may prevent osteoporosis and inhibit breast cancer growth in postmenopausal women.

Ospemifene, (Z)-2-[4-(4-Chloro-1,2-diphenyl-but-1-enyl)phenoxy]ethanol, which is one of the main metabolites of toremifene, is known as an estrogen agonist and antagonist (Kangas, Cancer Chemother. Pharmacol. (1990) 27:8-12; WO 96/07402 and WO 97/32574). Ospemifene has relatively weak estrogenic and antiestrogenic effects in the classical hormonal tests (Kangas, 1990). It has anti-osteoporosis actions and it decreases total and LDL cholesterol levels in both experimental models and in human volunteers. It also has antitumor activity in an early stage of breast cancer development in an animal breast cancer model. Ospemifene is also the first SERM which has been shown to have beneficial effects in climacteric syndromes in healthy women. The use of ospemifene for the treatment of certain climacteric disorders and atrophy-related diseases or disorders in postmenopausal women is disclosed in WO 02/07718 and WO 03/103649.

WO 01/36360 describes a group of SERMs, which are tissue-specific estrogens and which can be used in women in the treatment of climacteric symptoms, osteoporosis, Alzheimer's disease and/or cardiovascular diseases without the carcinogenic risk. Certain compounds can be given to men to protect them against osteoporosis, cardiovascular diseases and Alzheimer's disease without estrogenic adverse events (gynecomastia, decreased libido etc.). Of the compounds described in said patent publication, the compound (Z)-2-{2-[4-(4-chloro-1,2-diphenylbut-1-enyl)phenoxy]-ethoxy}ethanol (also known under the generic name fispemifene) has shown a very interesting hormonal profile suggesting that it will be especially valuable for treating disorders in men. WO 2004/108645 and WO 2006/024689 suggest the use of fispemifene for treatment or prevention of age-related symptoms in men, such as lower urinary tract symptoms and diseases or disorders related to androgen deficiency in men.

Known methods for the syntheses of compounds like ospemifene and fispemifene include rather many steps. WO 02/090305 describes a method for the preparation of fispemifene, where in a first step a triphenylbutane compound with a dihydroxy substituted butane chain is obtained. This compound is in a second step converted to a triphenylbutene where the chain is 4-chlorosubstituted. Then the desired Z-isomer is crystallized. Finally, the protecting group is removed to release the ethanol-ethoxy chain of the molecule.

In the known methods, the separation of the desired Z isomer is tedious. The protection group used to protect the ethanol-ethoxy chain during the reaction steps, benzyl, is rather difficult to remove.

SUMMARY

Both ospemifene and fispemifene are likely to be commercialized in the near future. Thus, there is a great need for powerful methods for the preparation of these compounds in large scale.

Another object is to provide methods having common features so that the syntheses of the compounds easily can be run by using the same kind of equipment and materials.

Thus, according to one aspect, this invention concerns a method for the preparation of a compound of formula (Ia) or (Ib):

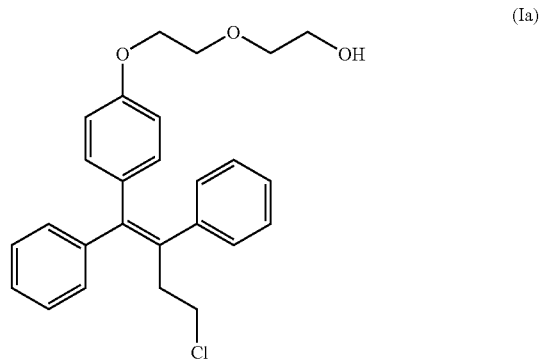

(Ia)

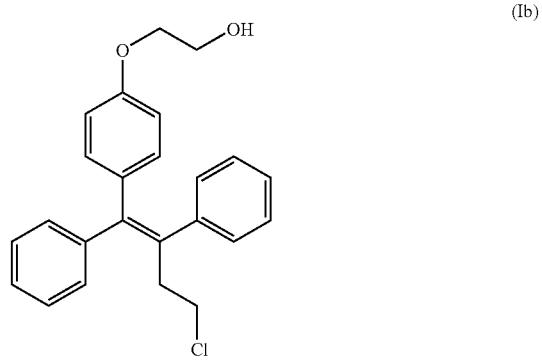

(Ib)

wherein a compound of formula (II)

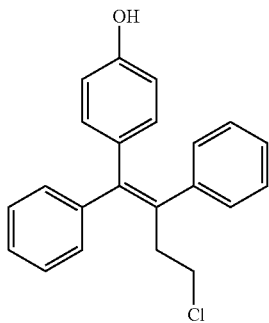

a) is alkylated with an alkylating reagent of the formula X—(CH$_2$)$_2$—O—(CH$_2$)$_2$—O—Pr,
where X is Cl, Br, I, mesyloxy or tosyloxy, and Pr is a protecting group, to give a compound of formula (III)

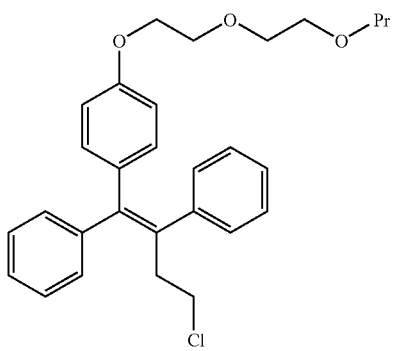

which is subjected to removal of the protecting group Pr to give the compound of formula (Ia), or b) is alkylated with an alkylating reagent of the formula X—(CH$_2$)$_2$—O—Pr, where X is Cl, Br, I, mesyloxy or tosyloxy, and Pr is a protecting group, to give a compound of formula (IV)

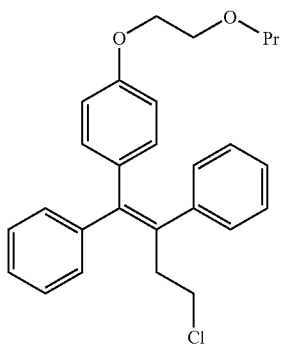

which is subjected to removal of the protecting group Pr to give the compound of formula (Ib), or c) is alkylated with an alkylating reagent of the formula X—CH$_2$—COOR, wherein X is Cl, Br, I, mesyloxy or tosyloxy, and R is an alkyl, to give a compound of formula (V)

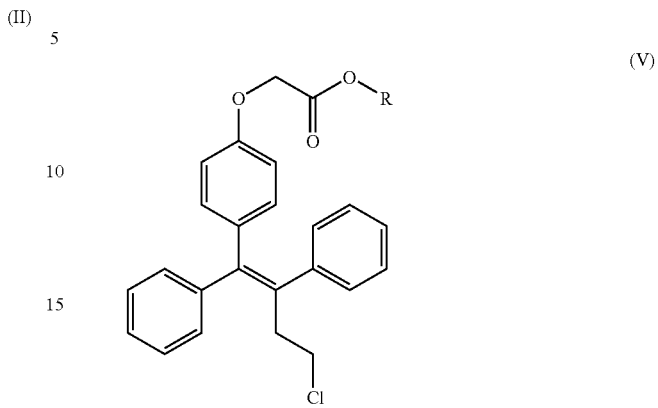

and the ester is reduced to give the compound of formula (Ib).

DETAILED DESCRIPTION

Fispemifene is the Z-isomer of the compound of formula (Ia)

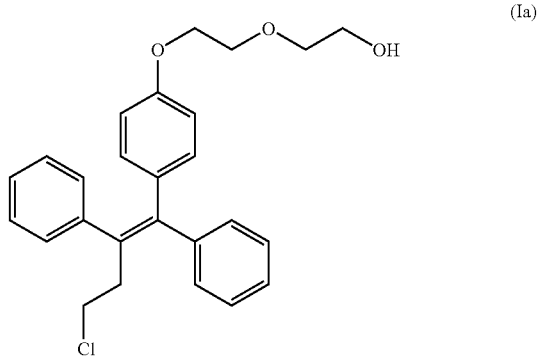

and ospemifene is the Z-isomer of the compound of formula (Ib)

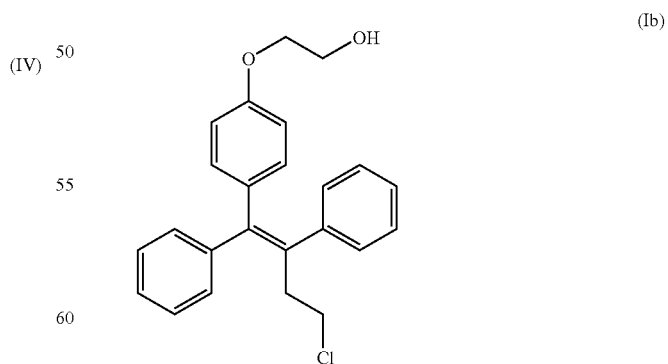

The common starting material in the syntheses of (Ia) or (Ib), namely compound (II), is previously known (Toivola, 1990; EP 0095875). According to a method disclosed in EP 095875, this compound was prepared by dealkylation of a corresponding ether to give (II). The method may be used to produce a mixture of isomers of compounds (Ia) and (Ib), but most preferably is used to prepare the pure E- and Z-isomers of those compounds.

Particularly in case Z-isomers of the compounds (Ia) or (Ib) are desired, a preferable method for the synthesis of compound (II) is a McMurry reaction of commercially available starting materials, 4-hydroxybenzophenone with 3-chloropropiophenone. The McMurry reaction is a well-known reductive coupling of ketones involving two steps: (1) a single electron transfer to the carbonyl groups from an alkali metal, followed by (2) deoxygenation of the 1,2-diol with low-valent titanium to yield the alkene. This reaction produces mainly the Z-isomer of compound (II).

The alkylation in steps a) and b) is carried out in an organic solvent, preferably carried out in tetrahydrofuran. It is also preferable to add a base to the solvent, most preferably sodium hydride.

The step of alkylation is performed at a temperature and a time to achieve substantial alkylation of compound II.

The protecting group Pr can be any suitable protecting group such as benzyl, substituted benzyl, allyl, tetrahydropyranyl or any other alcohol protecting group obvious to one skilled in the art; see for example Protecting Groups in Organic Synthesis, Third Edition, T. W. Greene and P. G. M. Wuts. Wiley Interscience, 1999 pp 23-200. In a preferable embodiment the protecting group is tetrahydropyranyl. This protecting group is very easily removable by methods known to those of ordinary skill in the art. For example, acid labile alcohol protecting groups such as a tetrahydropyranyl group (e.g., 2-tetrahydropyranyl) can be removed using acid such as HCl. A benzyl group can be removed using methods such as hydrogenation with Pd on carbon as a catalyst, or reacting with Zn powder and acetyl chloride.

X is preferably I or Br in the alkylating reagent in steps a) and b).

In the alkylating reagent in step c) X is preferably I, Br, or Cl, most preferably Br.

The alkyl substituent R in the alkylating reagent in step c) is preferably a $C_{1-4}$-alkyl, most preferably ethyl.

The reduction of compound (V) obtained in step c) is carried out with a reducing agent, preferably lithium aluminum hydride. Other reducing agents are well known to those of ordinary skill in the art.

The steps of the methods described herein are carried out at temperatures and for times sufficient to achieve the desired compounds (Ia) and (Ib). The selection of the parameters based on the disclosure herein can readily be made by one of ordinary skill without undue experimentation.

To sum up, the preferred embodiments according to the present invention provides considerable advantages over known methods for producing compounds of formula (Ia) or (Ib):

- The use of tetrahydrofuran as solvent and sodium hydride as a base in the alkylating steps a) and b) gives the desired products in good yields.
- The use of tetrahydropyranyl as protecting group is favorable because this protecting group is easy to remove leading to good yield of the product.
- The McMurry synthesis of compound (II) leads mainly to the Z-isomer. This is of particular importance when Z-isomers of the end products Ia and Ib are desired.

The invention will be illuminated by the following non-restrictive Examples.

Example 1

4-(4-Chloro-1,2-diphenyl-but-1-enyl)phenol (Compound II)

Zinc (15.0 g, 0.23 mol) and tetrahydrofuran (THF) (180 ml) was added to the reaction vessel and cooled to −10° C. Titan tetrachloride was added dropwise to the mixture (21.6 g, 0.114 mol) at about −10° C. After the addition was completed the mixture was refluxed for two hours. Then the mixture was cooled to 40° C. and 4-hydroxybenzophenone (7.68 g, 0.039 mol) and 3-chloropropiophenone (6.48 g, 0.039 mol) dissolved in THF (75 ml) were added to the mixture. Refluxing was continued for additional 3.5 hours. The cooled reaction mixture was poured in aqueous potassium carbonate solution (21 g $K_2CO_3$+210 ml water) and allowed to stand overnight at the ambient temperature. The mixture was filtered and the precipitate was washed with THF. The filtrate was evaporated to dryness. The residue was dissolved in ethyl acetate and washed with water. Ethyl acetate phase was evaporated to dryness and the residue was crystallized first from methanol-water (8:2) and then from methanol-water (9:1). Yield 5.4 g.

Z-isomer: $^1$H NMR (CDCl$_3$): 2.92 (t, 2H, =C$\underline{H}_2$CH$_2$Cl), 3.42 (t, 2H, =CH$_2$C$\underline{H}_2$Cl), 6.48 (d, 2H, aromatic proton ortho to hydroxy), 6.75 (d, 2H, aromatic proton meta to hydroxy), 7.1-7.4 (m, 10H, aromatic protons)

Example 2

2-(2-{2-[4-(4-Chloro-1,2-diphenyl-but-1-enyl)-phenoxy]ethoxy}-ethoxy)-tetrahydropyran (Compound III, where Pr is tetrahydropyranyl)

4-(4-Chloro-1,2-diphenyl-but-1-enyl)phenol (0.33 g, 0.001 mol) was dissolved in tetrahydrofuran (3 ml) under a nitrogen atmosphere. Sodium hydride (0.036 g, 0.0015 mol) was added to the solution and the mixture was stirred at room temperature for an hour. 2-[2-(2-iodo-ethoxy)-ethoxy)-tetrahydropyran (0.6 g, 0.002 mol) was added and the mixture was refluxed for 3 hours. After cooling and adding water the mixture was extracted three times with ethyl acetate. The organic phase was dried with sodium sulphate and evaporated to dryness. The residue was used in the next reaction step without further purification.

Example 3

2-{2-[4-(4-Chloro-1,2-diphenyl-but-1-enyl)-phenoxy]ethoxy}-ethanol (Compound Ia)

The residue of the previous reaction step (Example 2) was dissolved in ethanol (10 ml) and the solution was acidified with 2 N aqueous hydrogen chloride. The mixture was stirred over night at ambient temperature. Then the solvent was evaporated, water was added and the mixture was extracted three times with dichloromethane. The organic phase was washed with water, dried with sodium sulphate and evaporated to dryness. The residue was crystallized from heptane-ethyl acetate (8:2). Yield 0.216 g.

Z-isomer, $^1$H NMR (CDCl$_3$): 2.92 (t, 2H, =C$\underline{H}_2$CH$_2$Cl), 3.42 (t, 2H, =CH$_2$C$\underline{H}_2$Cl), 3.58-3.65 (m, 2H, OCH$_2$C$\underline{H}_2$OH), 3.7-3.82 (m, 4H, —C$\underline{H}_2$OC$\underline{H}_2$CH$_2$OH), 3.97-4.04 (m, 2H, ArOC$\underline{H}_2$—), 6.56 (d, 2H, aromatic proton ortho to hydroxy), 6.78 (d, 2H, aromatic proton meta to hydroxy), 7.1-7.43 (m, 10H, aromatic protons)

Example 4

2-[4-(4-Chloro-1,2-diphenyl-but-1-enyl)-phenoxy]-ethanol (Compound Ib)

4-(4-Chloro-1,2-diphenyl-but-1-enyl)phenol (0.23 g, 0.689 mmol) was dissolved in tetrahydrofuran (3 ml) under nitrogen atmosphere. Sodium hydride (0.025 g, 1.03 mmol) was added to the solution and the mixture was stirred at room temperature for an hour. 2-(2-iodo-ethoxy)-tetrahydropyran (0.3 g, 1.17 mmol) was added and the mixture was refluxed for 2 hours. Additional portions of 2-(2-iodo-ethoxy)-tetrahydro-pyran (0.5 g, 2 mmol) were added to the mixture during seven hours. After cooling and adding water, THF was evaporated and the mixture was extracted three times with ethyl acetate. The organic phase was washed with 2 N aqueous sodium hydroxide and water, dried with sodium sulphate and evaporated to dryness. The residue (which is Compound (IV) where Pr is tetrahydropyranyl) was dissolved in ethanol and acidified with 2 N aqueous hydrogen chloride solution. The mixture was stirred at room temperature over night, evaporated and extracted with dichloromethane. After washing with water the organic phase was dried ($Na_2SO_4$) and evaporated. The residue was purified by flash chromatography with dichloromethane/methanol 9.5/0.5 as eluent. Yield 0.17 g, 59%.

Z-isomer, $^1$H NMR ($CDCl_3$): 2.92 (t, 2H, =C$\underline{H}_2$CH$_2$Cl), 3.42 (t, 2H, =CH$_2$C$\underline{H}_2$Cl), 3.85-3.89 (m, 4H, OC$\underline{H}_2$C$\underline{H}_2$), 6.56 (d, 2H, aromatic proton ortho to hydroxy), 6.80 (d, 2H, aromatic proton meta to hydroxy), 7.1-7.43 (m, 10H, aromatic protons).

Example 5

2-[4-(4-Chloro-1,2-diphenyl-but-1-enyl)-phenoxy]-ethanol (Compound Ib)

The compound was prepared by the same method as described in Example 4 using 2-(2-iodo-ethoxymethyl)-benzene as a reagent and removing the benzylic protecting group using the method described in Example (e) of U.S. Pat. No. 6,891,070 B2, herein incorporated by reference. Briefly, the removal is carried out under a nitrogen atmosphere, in the presence of Zn powder and acetyl chloride.

Example 6

[4-(4-Chloro-1,2-diphenyl-but-1-enyl)-phenoxy]-acetic acid ethyl ester (Compound V where R is ethyl)

4-(4-Chloro-1,2-diphenyl-but-1-enyl)phenol (0.5 g, 0.0015 mol), absolute ethanol (10 ml), potassium carbonate (0.62 g, 0.0045 mol) and ethyl bromo acetate (0.373 g, 0.00224 mol) are mixed under nitrogen atmosphere and refluxed for 2.5 hours. Then the hot mixture was filtered and the precipitate was washed with absolute ethanol. The filtrate was evaporated, extracted with ethyl acetate and washed with water. Ethyl acetate was dried ($Na_2SO_4$) and evaporated to dryness. Yield 260 mg, 52%. The product was used without further purification in the next reaction step.

$^1$H NMR ($CDCl_3$+ MeOH—$_{d4}$): 1.25 (t, 3H, CH$_2$C$\underline{H}_3$), 2.92 (t, 2H, =C$\underline{H}_2$CH$_2$Cl), 3.42 (t, 2H, =CH$_2$C$\underline{H}_2$Cl), 4.22 (q, 2H, OC$\underline{H}_2$CH$_3$), 4.49 (s, 2H, ArOC$\underline{H}_2$—), 6.56 (d, 2H, aromatic proton ortho to hydroxy), 6.80 (d, 2H, aromatic proton meta to hydroxy), 7.1-7.43 (m, 10H, aromatic protons).

An alternative way to carry out the alkylation described in Example 6 is to replace absolute ethanol and potassium carbonate by sodium hydride and tetrahydrofuran. Preliminary experiments gave the product in high yield (90%) after a short reaction time (about 1 hour) at room temperature.

Example 7

2-[4-(4-Chloro-1,2-diphenyl-but-1-enyl)-phenoxy]-ethanol (Compound Ib)

[4-(4-Chloro-1,2-diphenyl-but-1-enyl)-phenoxy]-acetic acid ethyl ester (Example 7) was dissolved in tetrahydrofuran at room temperature under nitrogen atmosphere. Lithium aluminium hydride was added to the solution in small portions until the reaction was complete. The reaction was quenched by adding saturated ammonium chloride solution to the mixture. The product was extracted into toluene, which was dried and evaporated in vacuo. The yield 100 mg, 43%.

$^1$H NMR ($CDCl_3$): 2.92 (t, 2H, =C$\underline{H}_2$CH$_2$Cl), 3.42 (t, 2H, =CH$_2$C$\underline{H}_2$Cl), 3.85-3.89 (m, 4H, OC$\underline{H}_2$C$\underline{H}_2$), 6.56 (d, 2H, aromatic proton ortho to hydroxy), 6.80 (d, 2H, aromatic proton meta to hydroxy), 7.1-7.43 (m, 10H, aromatic protons).

It will be appreciated that the methods of the present invention can be incorporated in the form of a variety of embodiments, only a few of which are disclosed herein. It will be apparent to one of ordinary skill in the art that other embodiments exist and do not depart from the spirit of the invention. Thus, the described embodiments are illustrative and should not be construed as restrictive.

What is claimed is:

1. A method for the preparation of a compound of formula (Ib)

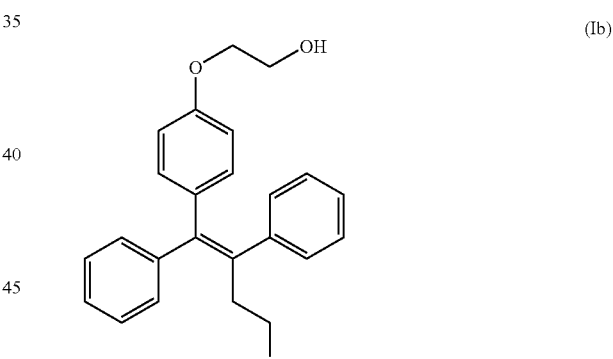

wherein a compound of formula (II)

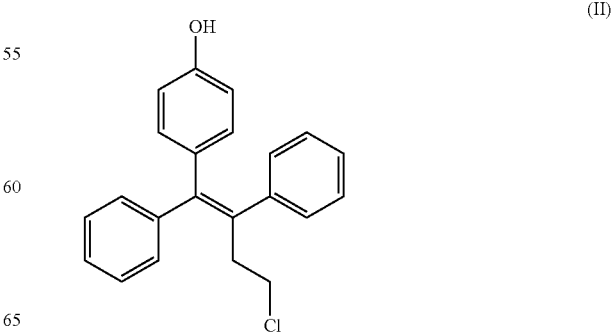

is alkylated with an alkylating reagent of the formula X—(CH$_2$)$_2$—O—Pr, where X is Cl, Br, I, mesyloxy or tosyloxy, and Pr is a protecting group, to give a compound of formula (IV)

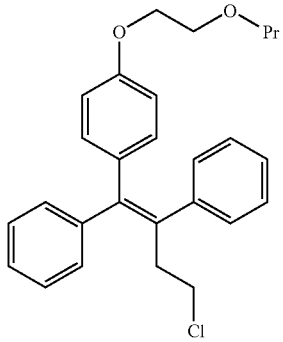
(IV)

which is subjected to removal of the protecting group Pr to give the compound of formula (Ib).

2. The method according to claim 1, wherein the compound of formula (II) is prepared by a McMurry reaction of 4-hydroxybenzophenone with 3-chloropropiophenone.

3. The method according to claim 1 or 2, wherein the alkylation is carried out in tetrahydrofuran.

4. The method according to claim 1, wherein the protecting group is tetrahydropyranyl.

5. The method according to claim 1 or 2, wherein the protecting group is benzyl.

6. The method according claim 1 or 2, wherein X in the alkylating reagent is I or Br.

7. A method for the preparation of a compound of formula (Ib)

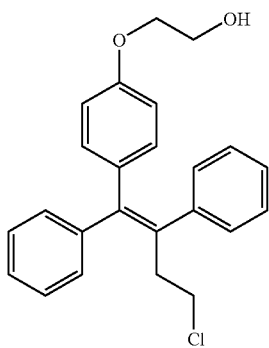

(Ib) comprising:
wherein a compound of formula (II)

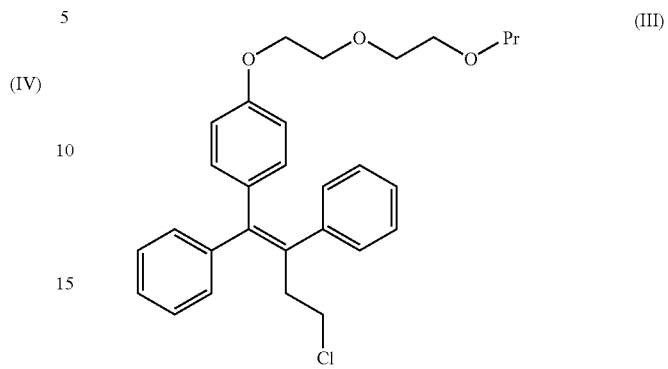
(III)

is alkylated with an alkylating reagent of the formula X—(CH$_2$)$_2$—O—Pr, where X is Cl, Br, I, mesyloxy or tosyloxy, and Pr is a protecting group, to give a compound of formula (IV)

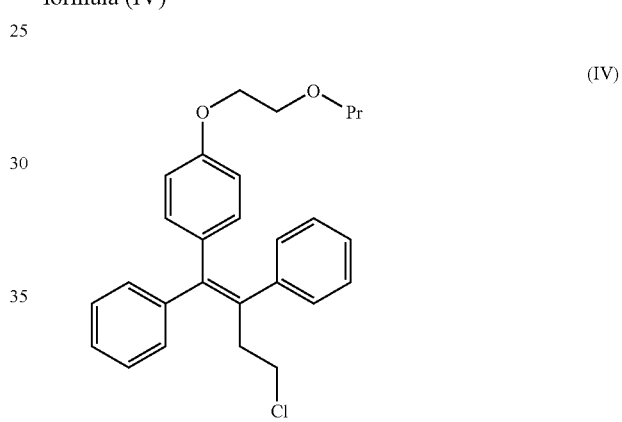
(IV)

which is subjected to removal of the protecting group Pr to give the compound of formula (Ib), wherein the compound (Ib) is the Z-isomer.

8. The method of claim 7, wherein X is I.

9. The method of claim 7, wherein Pr is tetrahydropyranyl or benzyl.

10. The method of claim 7, wherein Pr is 2-tetrahydropyranyl.

11. The method of claim 10, wherein the protecting group Pr is removed using acid.

12. The method of claim 9, wherein Pr is benzyl and is removed using zinc and acetyl chloride.

* * * * *

UNITED STATES PATENT AND TRADEMARK OFFICE
CERTIFICATE OF CORRECTION

PATENT NO.        : 7,812,197 B2                                        Page 1 of 1
APPLICATION NO.   : 12/030420
DATED             : October 12, 2010
INVENTOR(S)       : Sodervall et al.

It is certified that error appears in the above-identified patent and that said Letters Patent is hereby corrected as shown below:

In the Claims

In column 10, claim 7, replace the formula figure comprising lines 5 through 18 with:

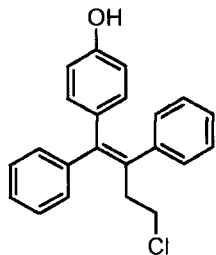

Signed and Sealed this
Sixteenth Day of August, 2011

David J. Kappos
*Director of the United States Patent and Trademark Office*